US008758238B2

(12) United States Patent
Clapp

(10) Patent No.: US 8,758,238 B2
(45) Date of Patent: Jun. 24, 2014

(54) HEALTH RELATED LOCATION AWARENESS

(75) Inventor: Geoffrey Clapp, Sunnyvale, CA (US)

(73) Assignee: Health Hero Network, Inc., Redwood City, CA (US)

(*) Notice: Subject to any disclaimer, the term of this patent is extended or adjusted under 35 U.S.C. 154(b) by 1863 days.

(21) Appl. No.: 11/643,116

(22) Filed: Dec. 21, 2006

(65) Prior Publication Data

US 2008/0059227 A1 Mar. 6, 2008

Related U.S. Application Data

(60) Provisional application No. 60/841,368, filed on Aug. 31, 2006.

(51) Int. Cl.
*A61B 5/00* (2006.01)
*G06Q 10/00* (2012.01)
*G06F 19/00* (2011.01)
*G06Q 10/06* (2012.01)

(52) U.S. Cl.
CPC ........ *G06F 19/30* (2013.01); *G06Q 10/063116* (2013.01); *G06F 19/322* (2013.01); *G06Q 10/063114* (2013.01); *G06Q 10/063112* (2013.01); *Y10S 128/92* (2013.01)
USPC ................ 600/300; 600/301; 128/920; 705/2

(58) Field of Classification Search
None
See application file for complete search history.

(56) References Cited

U.S. PATENT DOCUMENTS

| 3,808,502 | A | 4/1974 | Babilius |
| 3,910,257 | A | 10/1975 | Fletcher et al. |
| 4,110,918 | A | 9/1978 | James et al. |
| 4,173,971 | A | 11/1979 | Karz |
| 4,296,756 | A | 10/1981 | Dunning et al. |
| 4,428,733 | A | 1/1984 | Kumar-Misir |
| 4,625,733 | A | 12/1986 | Saynajakangas |
| 4,706,207 | A | 11/1987 | Hennessy et al. |
| 4,712,562 | A | 12/1987 | Ohayon et al. |
| 4,730,253 | A | 3/1988 | Gordon |
| 4,731,726 | A | 3/1988 | Allen, III |
| 4,749,354 | A | 6/1988 | Kerman |
| 4,751,642 | A | 6/1988 | Silva et al. |

(Continued)

FOREIGN PATENT DOCUMENTS

| EP | 0251520 | 1/1988 |
| EP | 0320749 | 6/1989 |

(Continued)

OTHER PUBLICATIONS

0000_00_00_American—Heritage_Dictionary—pa.

(Continued)

*Primary Examiner* — Gary Jackson
*Assistant Examiner* — Shirley Jian
(74) *Attorney, Agent, or Firm* — Suiter Swantz pc llo

(57) ABSTRACT

A remote health monitoring system, comprising a device suitable for transmitting and receiving data and configured for determining a geographic location of the device, a communication network and a server. The device is suitable for communicating with the server via the communication network, and a visitation schedule of a healthcare provider is determined based upon health related information of a patient and the geographic location of the device.

20 Claims, 6 Drawing Sheets

(56) References Cited

U.S. PATENT DOCUMENTS

| | | | |
|---|---|---|---|
| 4,757,022 A | 7/1988 | Shults et al. | |
| 4,803,625 A | 2/1989 | Fu et al. | |
| 4,835,372 A | 5/1989 | Gombrich et al. | |
| 4,838,275 A | 6/1989 | Lee | |
| 4,858,617 A | 8/1989 | Sanders | |
| 4,916,441 A | 4/1990 | Gombrich | |
| 4,995,402 A | 2/1991 | Smith et al. | |
| 5,019,974 A | 5/1991 | Beckers | |
| 5,033,474 A | 7/1991 | Varelis et al. | |
| 5,036,852 A | 8/1991 | Leishman | |
| 5,050,612 A | 9/1991 | Matsumura | |
| 5,077,476 A | 12/1991 | Rosenthal | |
| 5,137,028 A | 8/1992 | Nishimura | |
| 5,142,484 A | 8/1992 | Kaufman et al. | |
| 5,216,597 A | 6/1993 | Beckers | |
| 5,226,431 A | 7/1993 | Bible et al. | |
| 5,277,197 A | 1/1994 | Church et al. | |
| 5,307,263 A | 4/1994 | Brown | |
| 5,316,008 A | 5/1994 | Suga et al. | |
| 5,331,549 A | 7/1994 | Crawford, Jr. et al. | |
| 5,331,555 A | 7/1994 | Hashimoto et al. | |
| 5,336,245 A | 8/1994 | Adams et al. | |
| 5,339,821 A | 8/1994 | Fujimoto | |
| 5,357,427 A | 10/1994 | Langen et al. | |
| 5,359,509 A | 10/1994 | Little et al. | |
| 5,377,100 A | 12/1994 | Pope et al. | |
| 5,377,258 A | 12/1994 | Bro | |
| 5,381,138 A | 1/1995 | Stair et al. | |
| 5,390,238 A | 2/1995 | Kirk et al. | |
| 5,434,611 A | 7/1995 | Tamura | |
| 5,441,047 A | 8/1995 | David et al. | |
| 5,465,082 A | 11/1995 | Chaco | |
| 5,471,039 A | 11/1995 | Irwin, Jr. et al. | |
| 5,524,637 A | 6/1996 | Erickson | |
| 5,527,239 A | 6/1996 | Abbondanza | |
| 5,549,117 A | 8/1996 | Tacklind et al. | |
| 5,553,609 A * | 9/1996 | Chen et al. | 600/301 |
| 5,558,638 A | 9/1996 | Evers et al. | |
| 5,576,952 A | 11/1996 | Stutman et al. | |
| 5,596,994 A | 1/1997 | Bro | |
| 5,601,435 A | 2/1997 | Quy | |
| 5,659,793 A | 8/1997 | Escobar et al. | |
| 5,664,228 A | 9/1997 | Mital | |
| 5,678,571 A | 10/1997 | Brown | |
| 5,704,366 A | 1/1998 | Tacklind et al. | |
| 5,722,418 A | 3/1998 | Bro | |
| 5,732,709 A | 3/1998 | Tacklind et al. | |
| 5,812,983 A | 9/1998 | Kumagai | |
| 5,822,715 A | 10/1998 | Worthington et al. | |
| 5,828,943 A | 10/1998 | Brown | |
| 5,832,448 A | 11/1998 | Brown | |
| 5,868,669 A | 2/1999 | Iliff | |
| 5,879,163 A | 3/1999 | Brown et al. | |
| 5,887,133 A | 3/1999 | Brown et al. | |
| 5,893,098 A | 4/1999 | Peters et al. | |
| 5,897,493 A | 4/1999 | Brown | |
| 5,899,855 A | 5/1999 | Brown | |
| 5,913,310 A | 6/1999 | Brown | |
| 5,918,603 A | 7/1999 | Brown | |
| 5,933,136 A | 8/1999 | Brown | |
| 5,940,801 A | 8/1999 | Brown | |
| 5,950,632 A | 9/1999 | Reber et al. | |
| 5,951,300 A | 9/1999 | Brown | |
| 5,956,501 A | 9/1999 | Brown | |
| 5,960,403 A | 9/1999 | Brown | |
| 5,985,559 A | 11/1999 | Brown | |
| 5,997,476 A | 12/1999 | Brown | |
| 6,001,065 A | 12/1999 | DeVito | |
| 6,022,315 A | 2/2000 | Iliff | |
| 6,032,119 A | 2/2000 | Brown et al. | |
| 6,050,940 A | 4/2000 | Braun et al. | |
| 6,101,478 A | 8/2000 | Brown | |
| 6,144,837 A | 11/2000 | Quy | |
| 6,151,586 A | 11/2000 | Brown | |
| 6,161,095 A | 12/2000 | Brown | |
| 6,167,362 A | 12/2000 | Brown et al. | |
| 6,168,563 B1 | 1/2001 | Brown | |
| 6,177,940 B1 | 1/2001 | Bond et al. | |
| 6,186,145 B1 | 2/2001 | Brown | |
| 6,189,029 B1 | 2/2001 | Fuerst | |
| 6,196,970 B1 | 3/2001 | Brown | |
| 6,210,272 B1 | 4/2001 | Brown | |
| 6,233,539 B1 | 5/2001 | Brown | |
| 6,240,393 B1 | 5/2001 | Brown | |
| 6,246,992 B1 | 6/2001 | Brown | |
| 6,248,065 B1 | 6/2001 | Brown | |
| 6,260,022 B1 | 7/2001 | Brown | |
| 6,270,455 B1 | 8/2001 | Brown | |
| 6,330,426 B2 | 12/2001 | Brown et al. | |
| 6,334,778 B1 | 1/2002 | Brown | |
| 6,368,273 B1 | 4/2002 | Brown | |
| 6,375,469 B1 | 4/2002 | Brown | |
| 6,381,577 B1 | 4/2002 | Brown | |
| 6,847,892 B2 | 1/2005 | Zhou et al. | |
| 6,849,045 B2 | 2/2005 | Iliff | |
| 6,893,396 B2 * | 5/2005 | Schulze et al. | 600/300 |
| 6,968,375 B1 | 11/2005 | Brown | |
| 7,099,835 B2 * | 8/2006 | Williams, III | 705/27.1 |
| 7,154,397 B2 * | 12/2006 | Zerhusen et al. | 340/573.1 |
| 7,167,818 B2 | 1/2007 | Brown | |
| 7,168,818 B1 | 1/2007 | Schnell | |
| 7,249,036 B2 * | 7/2007 | Bayne | 705/2 |
| 7,252,636 B2 | 8/2007 | Brown | |
| 7,305,348 B1 | 12/2007 | Brown | |
| 7,570,152 B2 * | 8/2009 | Smith et al. | 340/286.07 |
| 7,711,582 B2 * | 5/2010 | Duckert et al. | 705/3 |
| 7,789,828 B2 * | 9/2010 | Clapp | 600/301 |
| 8,019,622 B2 * | 9/2011 | Kaboff et al. | 705/2 |
| 2001/0014863 A1 * | 8/2001 | Williams, III | 705/1 |
| 2002/0019584 A1 * | 2/2002 | Schulze et al. | 600/300 |
| 2005/0021369 A1 | 1/2005 | Cohen et al. | |
| 2005/0060198 A1 * | 3/2005 | Bayne | 705/2 |
| 2005/0108050 A1 | 5/2005 | Knapheide | |
| 2005/0131403 A1 * | 6/2005 | Massenzio et al. | 705/2 |
| 2006/0030890 A1 * | 2/2006 | Cosentino et al. | 607/5 |
| 2006/0036471 A1 * | 2/2006 | Sanjay-Gopal et al. | 705/3 |
| 2007/0040692 A1 * | 2/2007 | Smith et al. | 340/573.1 |
| 2009/0164236 A1 * | 6/2009 | Gounares et al. | 705/2 |
| 2010/0198608 A1 * | 8/2010 | Kaboff et al. | 705/2 |

FOREIGN PATENT DOCUMENTS

| | | | | |
|---|---|---|---|---|
| EP | 0353046 | | 10/1990 | |
| EP | 676709 A2 | | 10/1995 | |
| EP | 1622057 | | 2/2006 | |
| JP | 62-226278 | | 10/1987 | |
| WO | WO-93-02622 | | 2/1993 | |
| WO | WO-95-20199 | | 7/1995 | |
| WO | WO-95-29447 | | 11/1995 | |
| WO | WO-97-08605 | | 3/1997 | |
| WO | WO2013067159 A1 * | 5/2013 | | G08C 19/16 |

OTHER PUBLICATIONS

0000_00_00_American_Heritage_Dictionary_pe.
0000_00_00_Definition_of_Client_Server_from_PCMAG_COM.
0000_00_00_The_Merriam_Webster_Online_Dictionary_display.
0000_00_00_The_Merriam_Webster_Online_Dictionary_graphic.
0000_00_00_The_Merriam_Webster_Online_Dictionary_pictorial.
0000_00_00_The_Merriam_Webster_Online_Dictionary_symbol.
0000_00_00_The_Merriam_Webster_Online_Dictionary_symbolic.
0000_00_00_The_Merriam_Webster_Online_Dictionary_Video.
0000_00_00_Websters_Dictionary_II_com.
0000_00_00_Websters_Dictionary_II_con.
0000_00_00_Websters_Dictionary_II_i.

(56) References Cited

OTHER PUBLICATIONS

0000_00_00_Websters_Dictionary_II_m.
1978_11_00_Licklider_Applications_of_information_Networks_Proceedings_of_the_IEEE_vol._66_No._11.
1980_01_00_Haynes_Geriatrics_How_to_Detect_manage_Low_Patient_Compliance_in_Chronic_Illness.
1980_11_00_Haynes_Hypertension_Can_simple_Clinical_measurements_detect_patient_noncompliance.
1986_00_00_Physicians_Guide_Using_the_Health_Buddy_System.
1986_00_00_Thompson and Vandenberg, Clinical Biochemistry (1986) 19:255-261.
1987_06_02_U.S._Appl. No._07096998_Lee_Amendment.
1988_00_00_Hughes_Bedside_Terminals_Clinicom_MD.
1988_08_10_U.S._Appl. No._06879900_Fu_Amendment.
1989_00_00_Velho et. al., Biomed. Biochim. Acta (1989) 48(11/12):957:964.
1989_05_00_Paperny_Adolescent_Pregnancy_Prevention_by_Health_Education_Computer_Games_Computer_Assisted_Instruction.
1989_10_12_Diabcare Flyer Boehringer Mannheim HH101661-HH101668.
1990_00_00_Matthews_et_al_BMJ_Analysis_of_serial_measurement_in_medical_research.
1991_00_00_Diabcare User Manual HH007288-HH007331.
1991_07_23_Dept_of_Health_and_Human_Services_the_Physician_Guide_from_the_K864318_510K.
1992_00_00_Durant Medicine and Science in Sports and Exercise 24(2)265-271.
1992_11_17_07977323_Transmittal_Letter.
1993_00_00_Camit S Manual v3.00.
1994_05_00_Szolovits_Guardian_Angel_Patient_Centered_Health_Information_Systems.
1994_07_00_Genesereth_Software_Agents.
1995_08_10_Lai_Abstraction_Models_at_System_Level_for_Networked_Interactive_Multimedia_Scripting.
1995_09_01_Lunt_The_Smart_Cards_Are_Here.
1995_10_30_Mortorala_introduces_PCMCIA28.8_Modem.
1995_11_00_Hoffman_General_Purpose_Telemetry_for_Analog_Biomedical_Signals.
1996_00_00_Williams_Motivational_Predictors_of_Weight_Loss.
1996_07_12_llff_U.S._Appl. No._60021614.
2001_09_24_09300856_AMENDMENT.
2003_04_21_09422046_Amendment_with_Affidavit.
2005_06_13_11150145_Amendment.
2006_03_29_11150145_OA.
2006_06_19_09237194_Office_Actions_Response.
2006_06_26_11150145_Amendment.
2006_08_17_Abbott_v_Dexcom_06-514.
2006_08_17_Request_for_Re-examination_5899855_90008234.
2006_09_21_09237194_Declation_of_Stephen_Brown_with_Attached_Exhibits_Y_and_Z_thereof.
2006_09_22_11150145_OA.
2006_09_27_09422046_Office_Actions_Response.
2006_10_27_11150145_Amendment.
2007_01_04_11150145_Amendment.
2007_05_09_Leapfrog_v_Fisher_Price.
2007_10_29_Request_for_Re-examination_5899855_90008909.
2007_11_09_Request_for_Re-examination_7223236_90010053.
2007_11_15_Request_for_Re-examination_7223236_90010053.
2008_01_25_Dept_of_Health_and_Human_Services_The_Physicians_Guide_Become_publicly_Available.
2008_06_20_09422046_OA.
2008_06_20_Alere_First_Supplemental_Response_to_Plaintiff_Interrogatories.
2008_08_01_Excerpts_from_the_Prosecution_History_for_US_Patent_5899855.
2008_08_01_Inter_Party_Re-Exam_7223236_95000386.
2008_08_01_Request_for_Re-examination_5601435_90009237.
2008_08_01_Request_for_Re-examination_5879163_90009238.
2008_08_01_Request_for_Re-examination_6151586_90009240.
2008_08_01_Request_for_Re-examination_6161095_90009239.
2008_08_01_Request_for_Re-examination_7223236_95000386.
2008_09_23_Request_for_Re-Examination_6368273_90009281.
2008_12_04_Request_for_Re-Examination_5899855_90009352.
2008_12_10_Alere_Second_Supplemental_Response_to_Plaintiff_Interrogatories.
2008_12_10_Alere_Second_Supplemental_Response_to_Plaintiff_Interrogatories_Exhibit_1.
2008_12_10_Alere_Second_Supplemental_Response_to_Plaintiff_Interrogatories_Exhibit_2.
2008_12_10_Alere_Second_Supplemental_Response_to_Plaintiff_Interrogatories_Exhibit_3.
2008_12_10_Alere_Second_Supplemental_Response_to_Plaintiff_Interrogatories_Exhibit_4.
2008_12_10_Alere_Second_Supplemental_Response_to_Plaintiff_Interrogatories_Exhibit_5.
2008_12_10_Alere_Second_Supplemental_Response_to_Plaintiff_Interrogatories_Exhibit_6.
2008_12_10_Alere_Second_Supplemental_Response_to_Plaintiff_Interrogatories_Exhibit_7.
2008_12_10_Alere_Second_Supplemental_Response_to_Plaintiff_Interrogatories_Exhibit_8.
2008_12_10_Alere_Second_Supplemental_Response_to_Plaintiff_Interrogatories_Exhibit_8A.
2008_12_10_Alere_Second_Supplemental_Response_to_Plaintiff_Interrogatories_Exhibit_9.
2008_12_10_Alere_Second_Supplemental_Response_to_Plaintiff_Interrogatories_Exhibit_B.

* cited by examiner

HEALTH RELATED LOCATION AWARENESS

CROSS REFERENCE TO RELATED APPLICATIONS

The present application claims the benefit under 35 U.S.C. §119 of U.S. Provisional Application No. 60/841,368, filed on Aug. 31, 2006. Said U.S. Provisional Patent Application No. 60/841,368 is hereby incorporated by reference in its entirety.

FIELD OF THE INVENTION

The present invention generally relates to the field of remote health monitoring systems, and more particularly to remote health monitoring systems utilizing location-aware technology for improving in-home and mobile healthcare.

BACKGROUND OF THE INVENTION

Chronic health conditions and other long-term health issues are prevalent and expensive realities in the healthcare industry. Such health issues include heart disease, stroke, cancer, asthma, and diabetes. There is an increasing demand for in-home medical services to maintain satisfactory healthcare services, while reducing healthcare costs. These services may best be utilized for patients requiring frequent healthcare visits or monitoring. For instance, patients with chronic conditions may be placed on an in-home healthcare program utilizing preventative healthcare methods. Preventative healthcare methods promote the general well-being of patients and curtail the formation of costly medical conditions.

Preventative methods include patient education, periodic communication between the patient and the healthcare provider, and providing patients with tools or treatments for managing chronic conditions or patient behaviors. With these measures in place, patients may take an active role in their own healthcare and treatment. Additionally, when patients are able to frequently assess their condition, discrepancies from the usual condition may indicate the need to contact a healthcare provider. These contacts may prevent a potentially serious health condition from escalating and provide efficient healthcare to the patient. Thus preventative methods attempt to reduce the healthcare costs and avoid potentially tragic consequences of more serious health conditions. However, the success of a preventative treatment program often depends on the attitude of the patient and their willingness to participate in the recommended programs and methods. Thus, a patient-friendly program is desirable to maintain patient compliance with a specified preventative treatment program.

An in-home healthcare patient may have their condition monitored by a healthcare provider through use of a networked system for communicating information to the patient and remotely monitoring the patient. The system described in U.S. Pat. No. 6,968,375 is one such system to remotely monitor a patient's condition. Oftentimes, mobile healthcare providers are needed to provide various services and treatments directly to in-home patients. These services may be routine, on a need-based basis, or dynamically changing.

However, prior remote health monitoring systems do not sufficiently address many problems facing mobile healthcare providers and patients. First, healthcare providers must manage dynamic patient needs. For instance, in-home healthcare monitoring systems, such as Health Hero Network technologies, enable healthcare providers to oversee the condition of numerous patients simultaneously. Depending on individual patient needs, healthcare providers may be required to periodically visit patients within their homes for treatment, or visit patients within a controlled care setting, such as a hospital or assisted living facility. Healthcare providers may be faced with increasingly difficult scheduling demands as the number of patients utilizing in-home healthcare increases, or as the conditions of the patients change. For example, certain patients may require regular or routine in-home visits, but other patients may require in-home visits on a need-based basis or as per patient request. Thus, the traveling schedule for a healthcare provider may be continuously changing and dynamic. These scheduling demands may increase the administrative costs for in-home health care, thereby potentially offsetting the cost-saving benefits of in-home health care. Additionally, the efficiency of regularly scheduled in-home visits may be reduced through the dynamic nature of patient conditions, weather and traffic conditions, and other factors.

Second, in-home healthcare patients may require healthcare services while traveling such as when on business trips or vacations and may need to obtain healthcare supplies or testing while traveling. For instance, preventative treatment programs and other in-home medical treatments may require a patient to obtain medical supplies, treatments, tests, diagnostics, and other healthcare utilities located away from the patient's home. Patients may have difficulty determining what locations are appropriate for purchasing the supplies they require or for undergoing the proper tests. For example, a patient may have to spend a considerable amount of time calling healthcare companies and pharmacies to determine if they stock a specific medical supply, or visiting with various healthcare providers to determine what facility provides the requisite testing equipment, or simply attempting to find the lowest cost supplies, this may be especially beneficial for individuals in an unfamiliar area, such as when on vacation or traveling, and can assist patients in pricing supplies and determining the availability of supplies. Additionally, many in-home healthcare patients have limited mobility and are unable to travel significant distances to find the external services they require. This limitation may be the result of physical, economic, or other constraints, and obtaining external services can be difficult because of the need to schedule transportation. Furthermore, a patient may be an un-willing participant, thus it may be difficult to determine if the patient has consented to a desired regimen, for example, if they have attended physical therapy, an exercise session, and the like.

Thus, efficient and effective patient care demands a system that assists a healthcare provider to dynamically schedule in-home patient visits for patients undergoing a health monitoring program. Additionally, there is a demand for an efficient system to link in-home healthcare services with geographical information relevant to healthcare services.

SUMMARY OF THE INVENTION

Accordingly, the present invention is directed to a remote health monitoring system utilizing location-aware technology for optimizing in-home and mobile healthcare. In a present embodiment, the system includes a health related location awareness device configured for communicating with a server which stores and processes received device data. Device data includes patient query responses and location information. Patient query responses may be risk stratified and an optimized healthcare provider visitation schedule is created based upon the query responses received from multiple health related location awareness devices.

In another embodiment, the health related location awareness device is configured to display relevant healthcare locations. For instance, the device may communicate with the server or external communication network to obtain and display relevant healthcare locations, such as pharmacies, diagnostic centers, home healthcare supply outlets, and the like. The device can also be configured to display the location of grocery stores, department stores, and the like.

In yet another embodiment, the health related location awareness device is configured to track patient compliance. For instance, the device is configured to transmit geographic location data, which is compared to known geographic data for a particular healthcare location, such as a doctor's office. The device location data is then compared to the known healthcare location data, and where the two substantially overlap or intersect, it is assumed that the patient visited the healthcare location and was compliant with the healthcare program.

In a further embodiment, the healthcare provider visitation schedule includes information about healthcare supplies, such as medications, and pre-notifies the supplier of the upcoming visit by the care provider or patient. The pre-notification allows the healthcare supplier to prepare supplies for pickup before the healthcare provider or patient arrives at the store.

In a still further embodiment, the present invention includes a method for remote monitoring, producing a visit schedule, and displaying relevant locations via a health related location awareness device, allowing in-home healthcare providers to plan and prepare for appointments.

It is to be understood that both the foregoing general description and the following detailed description are exemplary and explanatory only and are not necessarily restrictive of the invention as claimed. The accompanying drawings, which are incorporated in and constitute a part of the specification, illustrate an embodiment of the invention and together with the general description, serve to explain the principles of the invention.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the presently preferred embodiments of the invention, examples of which are illustrated in the accompanying drawings.

Figure 1:
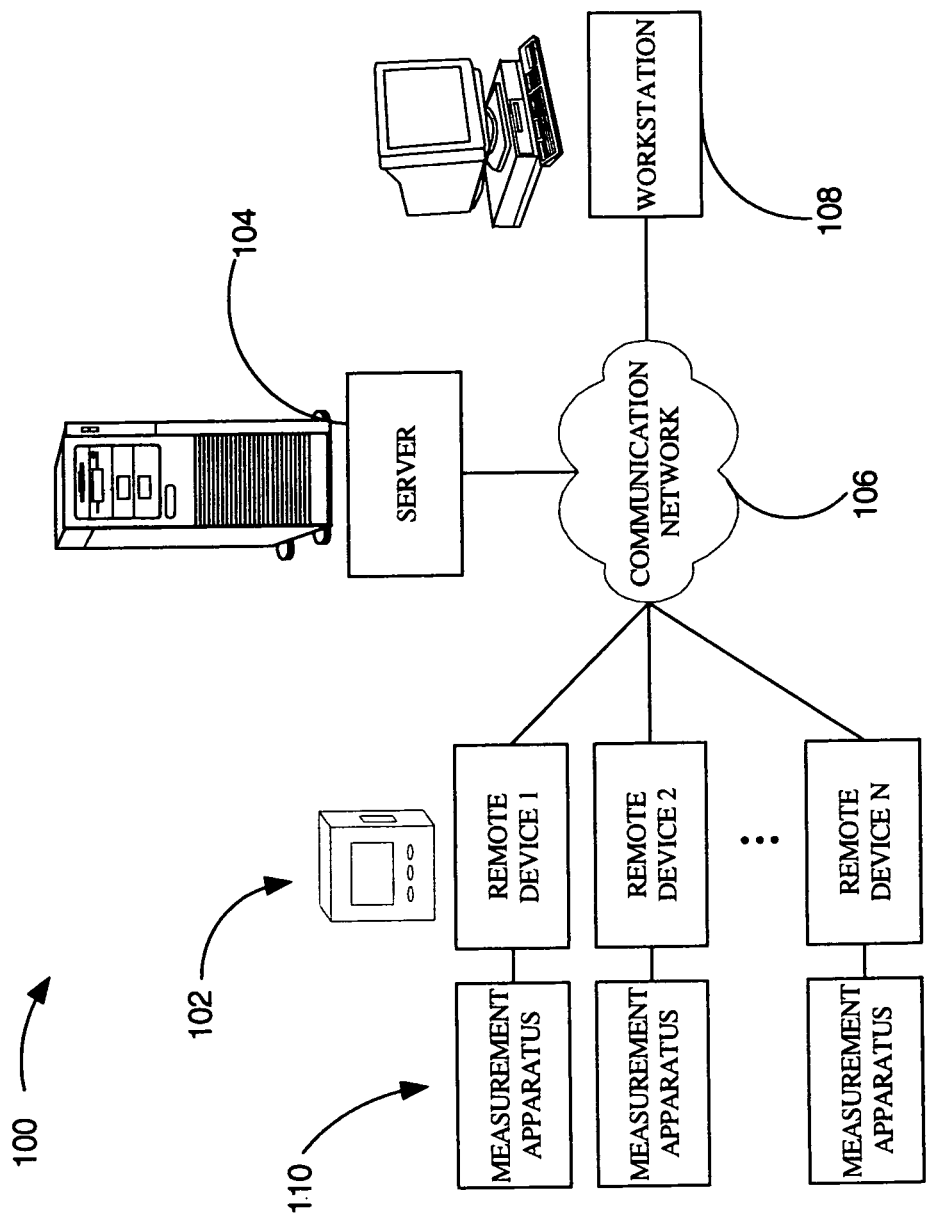
FIG. 1 is a block diagram of a health related location awareness system according to a present embodiment of the invention.

Referring now to FIG. 1, the present invention is directed to a health related location awareness system 100. In one embodiment, the health related location awareness system 100 includes a plurality of health related location awareness devices 102 configured for communicating with a server 104. A single health related location awareness device is hereinafter referred to as "device 102." The server 104 may store and process received device 102 data in addition to inputted programming information and other data communicated through a workstation 108. Communications between the device 102 and the server 104 and between the workstation 108 and the server 104 may be relayed via a communication network 106. For example, the communication network 106 is the Internet.

The workstation 108 may comprise a personal computer, remote terminal, or other remote interface apparatus suitable for communicating with the server 104 via the communication network 106. Various script programs, recommended patient activity, and other information as needed are inputted into the workstation 108, such as through a user interface. The communication network 106 then relays the inputted information to the server 104 where it is stored for later execution or processing. For instance, a script program includes queries requesting a patient response via the device 102. In a specific embodiment, the queries involve health related topics, such as questions regarding current health status, difficulty of regulating health factors (i.e., blood glucose level, blood pressure, etc.), and overall well-being. Similarly, recommended patient activities may be entered by a user upon review of patient responses to queries. For example, the user may be a healthcare provider recognizing that patient query responses indicate a need for a particular prescription medication. The healthcare provider may then input instructions into the workstation 108 via a user interface for the patient to obtain the medication. Healthcare providers may include Durable Medical Equipment installers (DME's), Homecare Nurses, and other practitioners who visit patients at home, at mobile locations, or at pharmacies. The device 102 additionally may be configured to display geographic information relevant to the patient, such as the nearest pharmacy supplying the medication; however this aspect of the invention will be discussed later.

Device may comprise

The device 102 may further comprise a measurement apparatus 110 such as. The measurement apparatus 110 may be suitable for measuring at least one of a blood glucose level, a pulse, a weight, a blood pressure, a peak flow, and other health measurements. In a current embodiment, script programs stored in the server 104 are relayed to the device 102 prompting a healthcare patient to connect to the measurement apparatus 110 of the device 102 and initiate a measurement. The device 102 may then transmit the measurement data to the server 104, to be analyzed either by programs or directly by a healthcare provider via a workstation 108. Alternatively, the patient may enter data manually and transmit the manually entered data to the server. To this end, device 102 may comprise at least one actuator for inputting a response to a query. Also, the device 102 may be configured for tracking patient compliance with a healthcare management program via data received from the measuring apparatus 110.

The device 102 additionally includes location-aware technology adapted for transmitting the geographical location of the device 102 and for manipulating geographical information about other relative locations. Location-aware technology may include GPS, Radio Frequency Identification (RFID), and Personal Local Area Networks (PLAN) and Wireless Local Area Networks (WLAN), such as 802.11, Wi-Fi, and Bluetooth, or other suitable technology, or combination of these technologies. Suitable location-aware technology provides functional geographic or relational data configured for location determination. Such technology is desirable for mobile devices where location information may frequently change. The location-aware technology may be configured to report geospatial position data in near real-time, or alternatively, may be configured to report geospatial position data upon request, such as upon patient acknowledgement for patient privacy consideration and/or availability for visitation. For example, where geospatial position data is only available to a healthcare provider upon patient disclosure (i.e., the patient voluntarily allows geospatial position data to be sent from the device 102), the healthcare provider can avoid visiting patients who do not consent to revealing their location or who are unavailable for a visit. Thus, the efficiency of the healthcare provider visitation schedule is not hindered by visiting unavailable patients. Voluntary patient data release may be best for patients with less-than-serious chronic conditions and low health risks if a healthcare provider is not allowed to access geospatial position data continuously. The device 102 incorporated in the present invention may communicate device location to the server 104 via the communication network 106.

Device location is significant relative to multiple embodiments of the current invention. For instance, the present invention may utilize device location as a component or variable of a visit schedule program. In a current embodiment, the server 104 implements a visit schedule program designed to generate an optimized route for a healthcare provider to visit in-home healthcare patients. The visit schedule program utilizes a data mining procedure to risk stratify patients. For example, patient responses to queries received by the device 102, patient availability, internet traffic reports, internet weather reports, and estimated needed for each visit form the basis for datasets. To this end, device 102 may be configured receive input patient availability data and transmit the patient availability data to a server. Device may also be configured for receiving a query from the server, displaying the query on an interactive display of the device, accepting a patient query response, and transmitting the patient query response to the server. The datasets are then analyzed to determine which patients require the most urgent care or are the highest priority to visit, such as by which responses deviate the most from an ideal health condition or where a negative health trend is indicated. Additional data, such as a patient request for a visit, a trend of data over time, or educational planning may also be included in the datasets as factors for stratifying patients. The patients are then prioritized relative to the preferred data categorization or urgency of required in-home healthcare methods. The location of a particular individual (e.g., an in-home healthcare patient) may be attributed to device location, such that an individual's location is approximated by the device location, or the patient can manually enter their location. It is desirable that the device 102 size not substantially hinder an individual's ability to use the device 102 as a portable article (i.e., take the device 102 wherever they go). An easily portable device 102 may assist with patient compliance, especially where the burden of transporting the device 102 is low. Thus, the individual location as device location approximation may be more accurate. Device location data then may be correlated with patient order, providing a list of geographic locations for a mobile healthcare provider to visit. Thus, a visitation schedule is produced. Healthcare providers therefore have access to data including risk stratification, notification of a supply need, as well as location information for all patients via the workstation 108 connection with the server 104.

Figure 2:
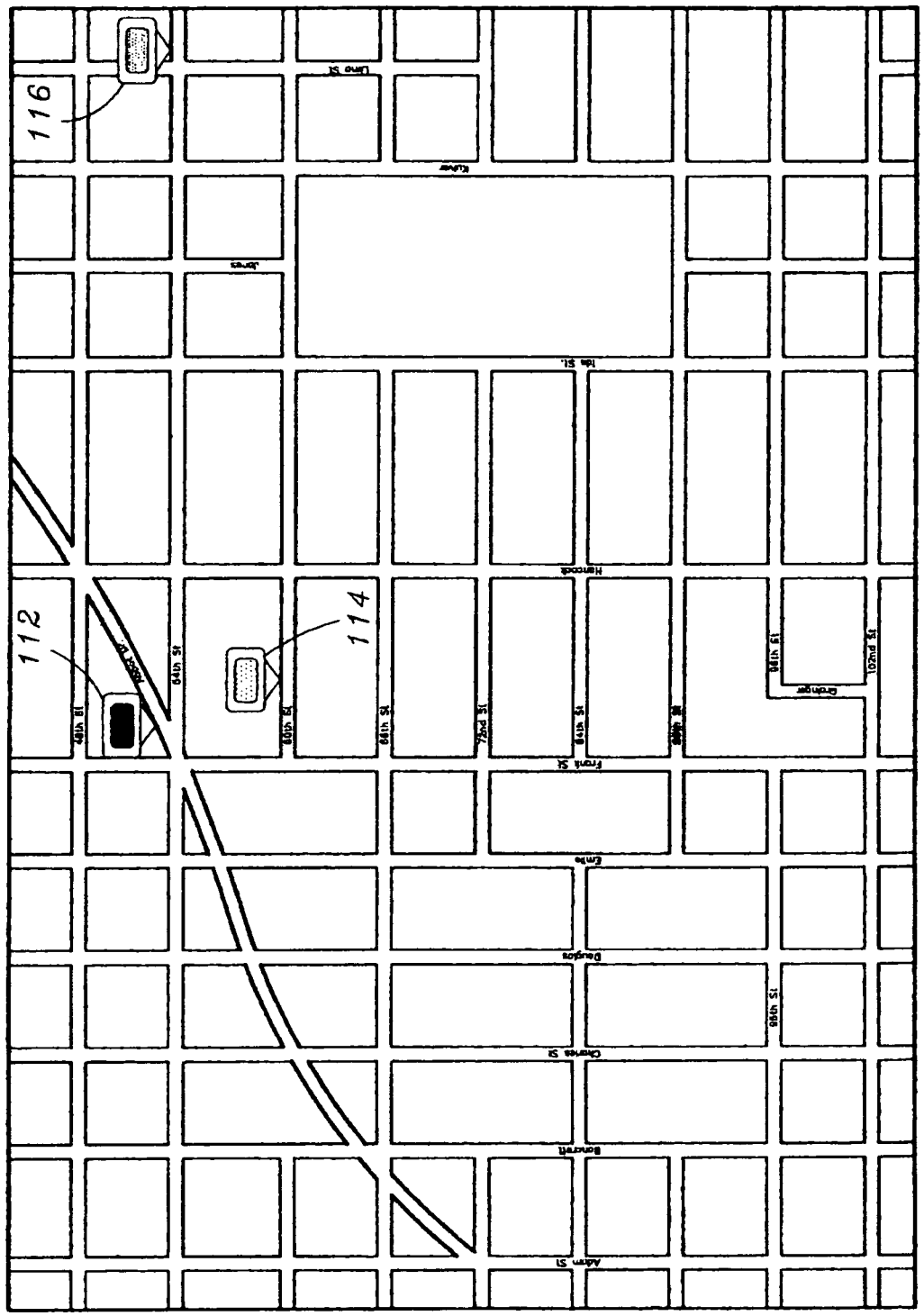
FIG. 2 is an exemplary map view of locations of patients with varying priority visitation levels.

However, depending on patient location and patient priority order, a straightforward "down-the-list" scheduling algorithm may be inefficient. Patient location and priority may require a healthcare provider to travel undesirable distances between patients, such that the healthcare provider bypasses a patient in need of a healthcare visit, but is not scheduled as the subsequent priority in the stratification list. Thus, the overall patient visitation time, selected as the time taken to visit all patients on the priority list, may be inefficiently high. For example, referring to FIG. 2, an exemplary map view of locations of three patients with varying priority visitation levels is shown. A first patient 112 and a third patient 114 (relative to priority order stratification) may be located substantially close to each other, whereas a second patient 116 may be located substantially distant from the first patient 112 and the third patient 114. Thus, it may be undesirably inefficient for the healthcare provider to visit the patients according to priority order, since the overall patient visitation time would be lower by visiting the first patient 112 and then the third patient 114 prior to visiting the second patient 116. However, the priority order selected according to a preferred data categorization (e.g., urgent patient health condition, patient visit request, patient education, and the like) may still influence a visitation schedule. For instance, it may not be desirable to implement a visitation schedule solely based on geographical convenience, such as when patients with urgent needs, as compared to the remainder of the priority list, are located a significant distance apart. Therefore, a variety of scheduling algorithms may be used to improve or optimize the healthcare provider visitation schedule. For example, the scheduling algorithm may include a greedy algorithm (i.e., shortest tasks performed first), decreasing time algorithm, critical-path algorithm, traveling salesman algorithm (i.e., an algorithm optimizing the commonly known traveling salesman problem), real-time scheduling algorithm, genetic algorithm, or other suitable scheduling algorithm.

Device location data provided by the location-aware technology may be manipulated to create an accurate and user-friendly visitation schedule. In a present embodiment, device location data transmitted from the device 102 to be stored in the server 104 is retrieved and converted into latitude and longitude data. The server 104 may run a geocoding program to implement geocoding interpolation techniques to derive sets of latitude and longitude coordinates for the patients based on device location. The geocoding program may be a commercially available program, an open-source program, or customized for specific needs. For example, the geocoding program accesses the TIGER On-Line Mapping Resource (Topologically Integrated Geographic Encoding and Referencing system) provided by the United States Census Bureau, where most United States addresses are converted into latitude and longitude coordinates. The geocoding program may then display the coordinates in a user-friendly format (i.e., relatively simple for an average user to understand), such as a map display.

Figure 3:
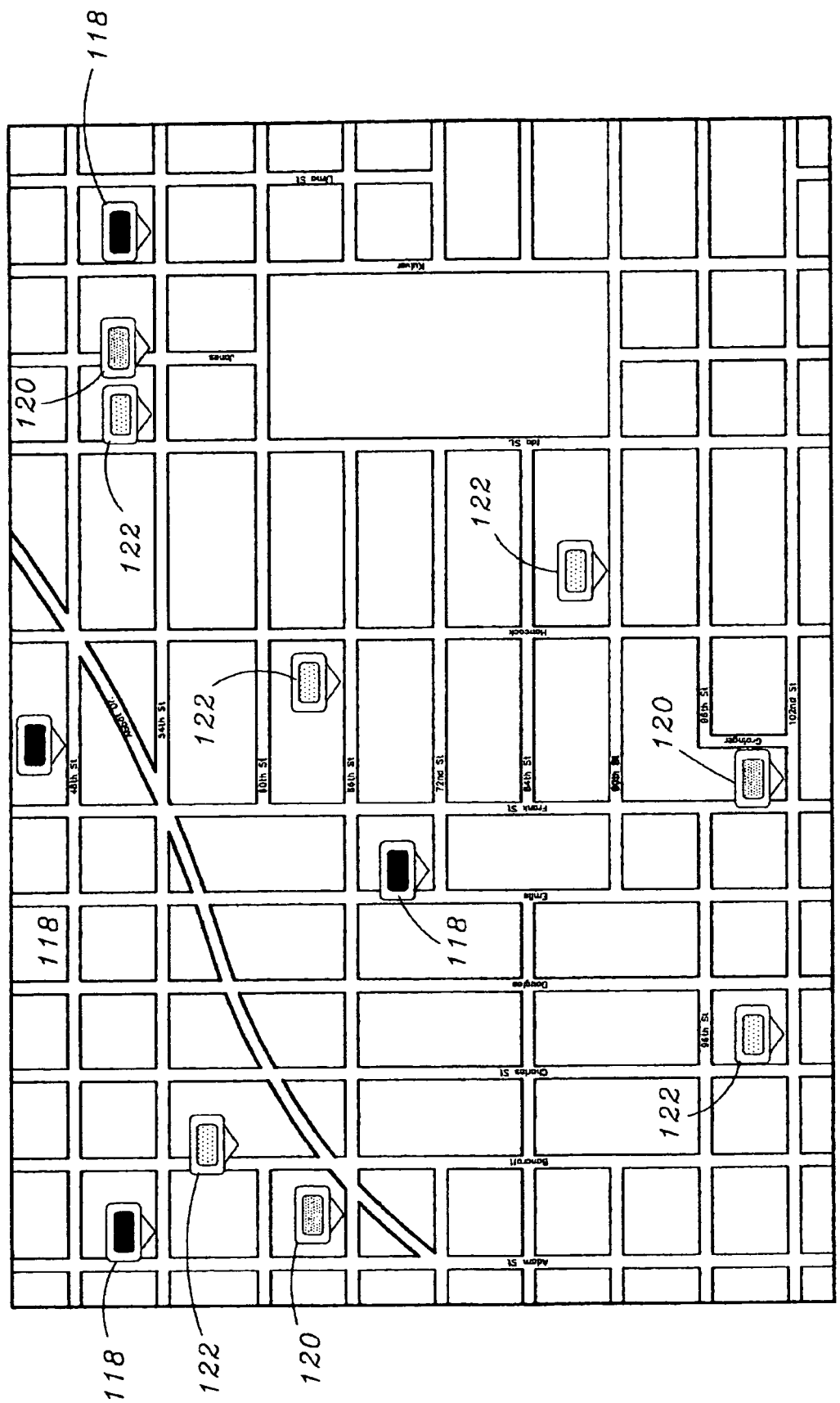
FIG. 3 is an exemplary patient risk stratification priority list plotted on a map, wherein the priority list and map formulate a healthcare provider visitation schedule generated according to one embodiment of the present invention.

In a specific embodiment, the geocoding program utilizes Yahoo!® or Google® Maps via the communication network 106 (e.g., the Internet) to display the coordinates in a user-friendly format. An exemplary patient risk stratification priority list map is depicted in FIG. 3. In one embodiment of the current invention, patients may be risk stratified into three groups. The first group may correspond to high risk patients 118, the second group may correspond to medium risk patients 120, and the third group may correspond to low risk patients 122. The desired algorithm may then produce a healthcare provider visitation schedule based on risk stratification and respective patient location. Location-aware technology enables patient location information to not be constrained to a static database of residence locations, but can be dynamically updated through use of the device 102. Therefore the present invention can extend the care-providing network to business travelers, vacationers, patients requiring emergency services, and other patients not located at a "home" or residence location.

The health related location system 100 may further utilize additional external data in the formulation and/or alteration of the healthcare provider visitation schedule. In a present embodiment, the health related location system employs traffic data to develop and/or alter the healthcare provider visitation schedule, as desired for optimization, convenience, and the like. The traffic data may be available via a Web-based data site. For instance, the server 104 may access a Web-based traffic data site via the communication network 106 and utilize respective traffic information in scheduling algorithms. The traffic data may be utilized during creation of a visit schedule, or alternatively, may be utilized to alter an existing visit schedule. For example, the health related location awareness system 100 derives a mobile healthcare provider visitation schedule progressing from a first patient, A, then to a second patient, B, then to a third patient, C, and finally to a fourth patient, D. Traffic data, such as that received from a Web-based traffic data site, may indicate a road constriction or closure due to an accident, construction, disabled vehicle, and the like, whereby the originally prescribed route from B to C is either impossible to take or substantially hindered. The scheduling algorithm may then factor in the real-time traffic data and alter the visitation schedule from ABCD to ACBD for overall patient visitation time efficiency and healthcare provider convenience. Thus the inefficiencies of traffic can be abated before substantially delaying mobile healthcare services. Similarly, the health related location system may utilize weather information in the formulation and/or alteration of the healthcare provider visitation schedule. Weather information may be particularly relevant for mobile healthcare providers servicing a relatively large area, where variable weather patterns may impede travel to certain locations, while routes to other locations are unaffected.

After a visitation schedule is formulated, the health related location system 100 may be configured to report to a patient their relative order in a patient visitation schedule, or alternatively, an approximate visitation time by a mobile healthcare provider. Patients may view the report utilizing device 102. For example, a patient receives a message on device 102 stating a patient visit number out of total patients (e.g., patient number 5 of 9) or an approximate visitation time (e.g., 3:30 p.m.). Additionally, where traffic, weather, or some other condition affects patient visitation order or time, the health related location awareness system 100 may be configured to provide the patient with an alert and/or an updated visitation order or time. Thus, patient care may be enhanced by providing patients with accurate knowledge of patient care visits, including updated scheduling changes.

The health related location awareness system 100 may account for multiple routes or travel paths while devising healthcare provider visitation plans. These routes or travel paths may include city and county roads, interstates, highways, freeways, turnpikes, expressways, bridges, tunnels, and the like, and may cross reference public transportation options, such as buses, trains, subways, and the like.

Figure 4:
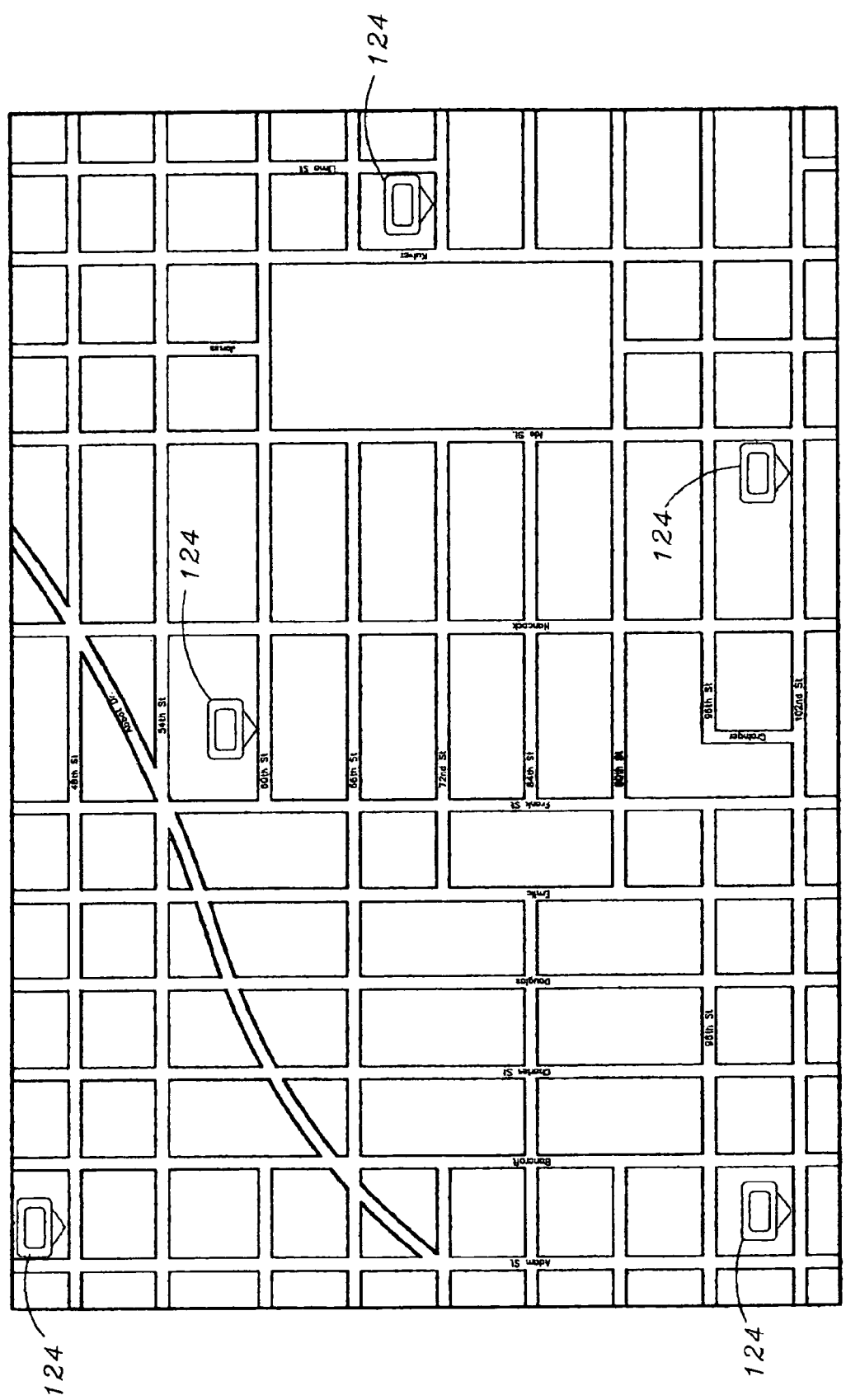
FIG. 4 is an exemplary patient perspective map generated according to another embodiment of the present invention, wherein the pin-points represent healthcare service locations.

Referring now to FIG. 4, a patient perspective map of healthcare service locations 124 is shown. In a current embodiment, the device 102 displays geographic location information of relevant healthcare service locations 124 to a user of the present invention (e.g., an in-home healthcare patient). Relevant healthcare service locations 124 may include pharmacies, diagnostic centers, home healthcare supply outlets, physician offices, insurance and governmental assistance locations, and the like. The server 104 of the health related location awareness system may store a multitude of geographic location information of various healthcare service locations 124 in the form of a database or a plurality of databases collectively referred to as a healthcare location database. For example, known healthcare locations may be inputted into a workstation 108 for storage in the server 104, or alternatively, healthcare locations may be equipped with location-aware technology configured to submit location information to the server 104. In one embodiment, the healthcare location database is accessed by a healthcare location program. The healthcare location program may be designed for providing a user of the device 102 with relevant information about the location of healthcare utilities. For instance, the healthcare location program searches the database for the pharmacy nearest a particular user having a specific prescription medication. To determine the nearest location, the healthcare location program may perform a twofold operation: first, select those pharmacies which stock the prescription medication (or have ready access to the medication), and second, compare the locations of the chosen pharmacies with the location of the particular device location and select the closest pharmacy in terms of geographical distance or travel distance. The first operation portion may additionally search for particular brand names, cost, availability, and the like, to provide enhanced patient care. It is appreciated that the healthcare location program operates to determine convenient locations (e.g., closest geographical location providing healthcare goods and/or services) of healthcare services in addition to prescription carriers, such as physician offices, diagnostic centers, home healthcare supply outlets, insurance and governmental assistance locations, and the like.

Alternatively, the second operation portion may select a plurality of locations to be displayed to a user. This functionality is desirable when a number of locations have or have access to a particular healthcare product or service at the same general level of availability, cost, etc, such as a specific chain of pharmacies, for example. Thus, a patient may have the option of choosing a preferred location from a list of relevant and adequate locations to obtain healthcare services and/or products, rather than limiting the choice to an algorithm-defined "best" location.

In addition to plotted latitude and longitude locations, geographic data displayed by device 102 may include city and county roads, interstates, highways, freeways, turnpikes, expressways, bridges, tunnels, and the like, and may cross reference public transportation options, such as buses, trains, subways, and the like.

The health related location awareness system of the present invention may additionally include a patient compliance tracking aspect. The success of in-home healthcare and preventative treatment programs often depends on patient attitude and their willingness to participate in the recommended programs and methods. Thus, it may be desirable for a healthcare provider to track the compliance of a patient to ensure adequate healthcare is available to the patient. For instance, if a patient is unwilling to participate in a healthcare program, a healthcare provider may reinforce the objectives of the program with the patient to provide another opportunity to comply with the program and offer enhanced healthcare. In one embodiment, the patient compliance tracking is accomplished by comparing device location data with known or programmed healthcare service location data. This comparison may be executed by a compliance program stored in the server 104. Where the device location data and healthcare service location data substantially overlap or intersect, it may be assumed that the patient visited the healthcare service location and, thus, was compliant with the healthcare program.

In a further embodiment, the healthcare provider visitation schedule is augmented with information on supplies, such as medications, and pre-notifies the supplier of the upcoming visit by the care provider or patient. Healthcare services may utilize a remote terminal or device 102 configured to communicate supply and/or service data with the health related location awareness system of the present invention. It may be desirable to notify suppliers of goods and/or services of an upcoming visit by a healthcare provider or a patient, such as when patient responses to queries on the device 102 indicate a need for healthcare supplies or services. Such a notification process may ensure the availability of particular goods or services upon healthcare provider or patient arrival, or to expedite the acquisition process. For example, a pharmacy may have access to a remote interface, such as workstation 108 or similar remote interface apparatus configured to present relevant healthcare supply information via the health related location awareness system.

Figure 5:
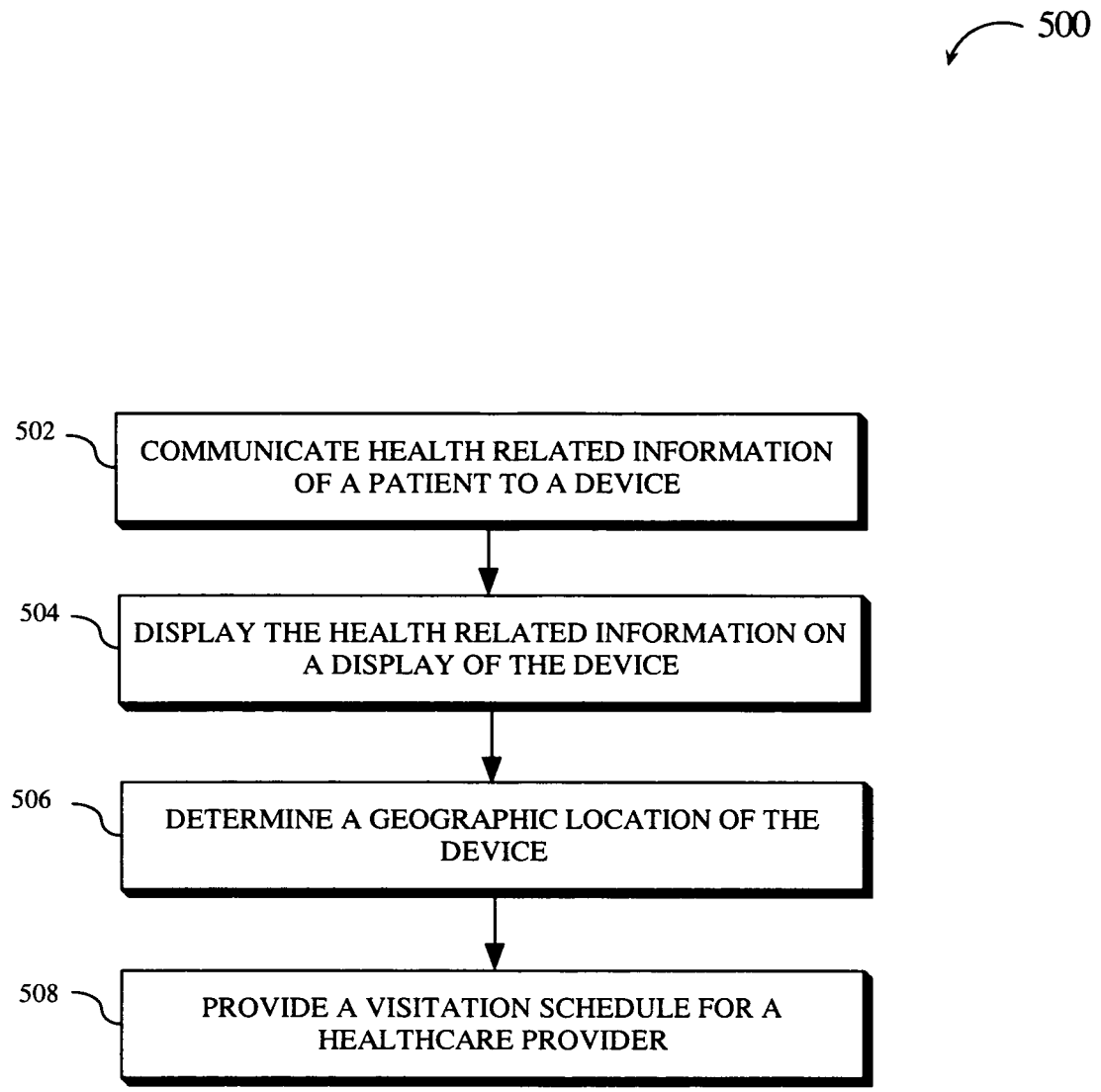
FIG. 5 is a flow diagram illustrating a method for remote health monitoring in accordance with an exemplary embodiment of the present invention.

Referring to FIG. 5, a flow diagram representing a method 500 for remote monitoring, producing a visit schedule, and displaying relevant locations via a health related location awareness device is shown. Method 500 may comprise communicating health related information of a patient to a device 502, displaying the health related information of a patient on a display of the device 504, determining a geographic location of the device 506, and providing a visitation schedule for a healthcare provider 508 based on the health related information of a patient and the location of the device.

Method 500 may further comprise determining a location of a healthcare facility in proximity to the device and displaying the healthcare facility location via the health monitoring device. The healthcare facility may comprise at least one of a pharmacy, a diagnostic center, a home healthcare supply outlet, a physician office, or an insurance and governmental assistance location. Method 500 may further comprise verifying a supply inventory of the healthcare facility and determining patient availability for a visit from said healthcare provider. Method 500 may also comprise determining patient compliance with a healthcare program. Providing a visitation schedule 508 may be determined by at least one of patient availability, a patient response to a query, a measured health parameter, severity of patient condition, patient geographic location, a web based traffic report, a web based weather report, or educational planning. Determining a geographic location for the device may be accomplished via at least one of a global positioning system, a wireless location area network, a wireless personal area network, or a radio frequency identification system.

Figure 6:
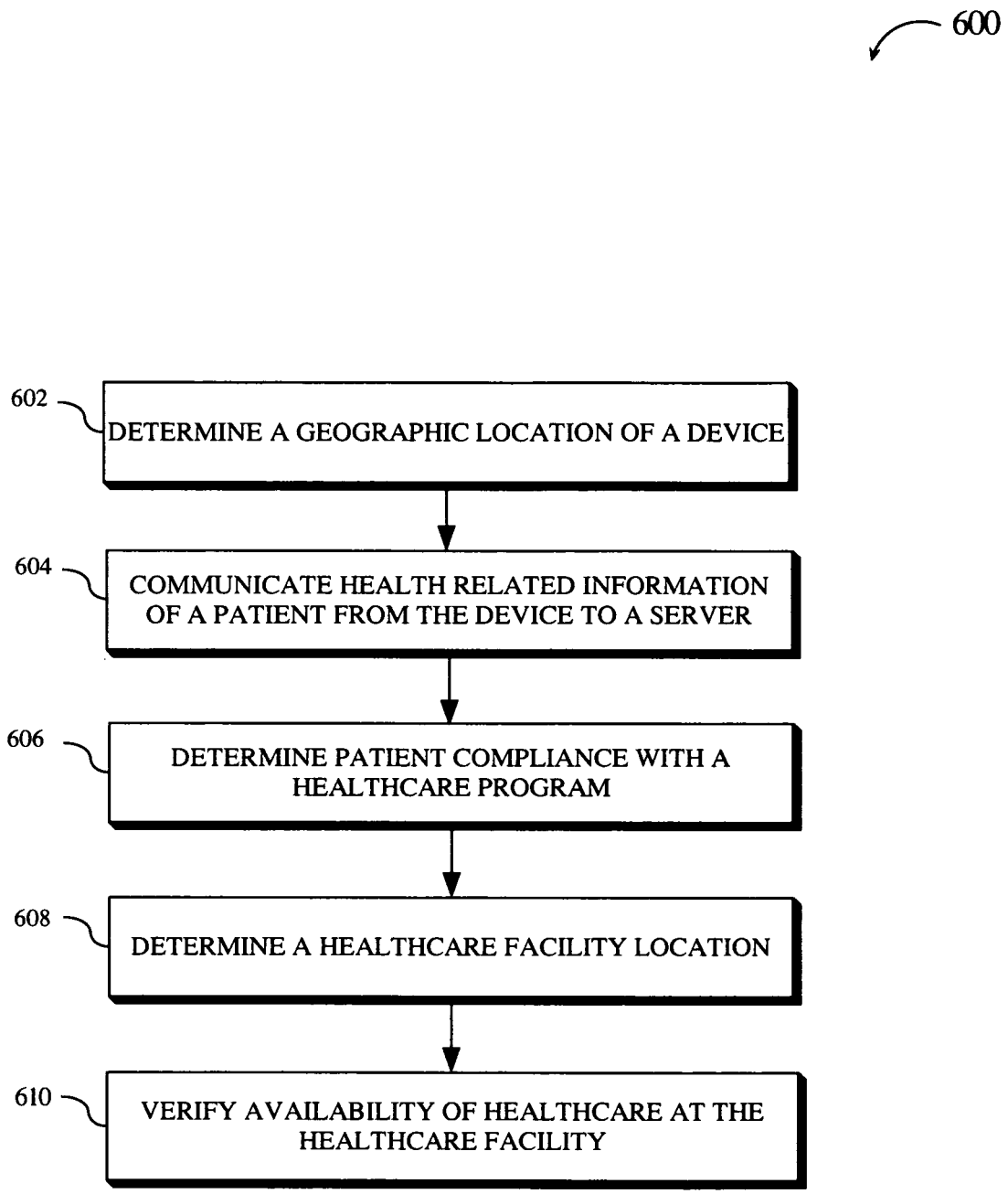
FIG. 6 is a flow diagram illustrating an additional embodiment of a method for remote health monitoring in accordance with an exemplary embodiment of the present invention.

Referring to FIG. 6, a flow diagram illustrating a method 600 for remote health monitoring is shown. Method 600 may comprise determining a geographic location of a device 602, communicating health related information of a patient from the device to a server 604, determining patient compliance with a healthcare program 606, determining a healthcare facility location 608 and verifying availability of healthcare at the healthcare facility 610. The healthcare may be a medical supply, diagnostic test or medical treatment, and the like. Method 600 may further comprise displaying said healthcare facility location on said device. The healthcare facility may be at least one of a pharmacy, a diagnostic center, a home healthcare supply outlet, a physician office, or an insurance and governmental assistance location. Method 600 may further comprise measuring health related data. The health related data may be at least one of a blood glucose level, a pulse, a weight, a blood pressure, or a peak flow and the like. Method 600 may further comprise determining patient availability for a visit from a healthcare provider. Determining a geographic location for the device 602 may be accomplished via at least one of a global positioning system, a wireless location area network, a wireless personal area network, or a radio frequency identification system.

In one embodiment, remote monitoring may be accomplished through use of a remote monitoring system, such as that disclosed in U.S. Pat. No. 6,968,375. Location-aware technology is utilized in conjunction with the remote monitoring system to provide patient and healthcare service location data. The location aware technology may operate on a real-time basis or may report patient location only with patient consent, such as for privacy reasons. The patient risk levels are then stratified according to patient responses to queries received by the device 102 and according to other data, such as patient requests for visits, educational planning, and the like. A suitable scheduling algorithm process patient location and risk stratification data to produce a healthcare provider visit schedule. The schedule may be updated continuously or periodically, depending on the frequency of reporting patient location. Further, the health related location awareness system provides a patient with geospatial location information of healthcare services relevant to particular patient needs, such as pharmacies, diagnostic-centers, clinics, and the like.

It is believed that the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A remote health monitoring system, comprising:
at least two data transmitting and receiving devices, each data transmitting and receiving device of said at least two data transmitting and receiving devices includes a global positioning system receiver, said global positioning system receiver determines a geographic location of said device, each data transmitting and receiving device transmits said geographic location of said device, each data transmitting and receiving device being associated with a single patient and includes at least one actuator for data input for responding to a health related information query, each data transmitting and receiving device providing patient availability, and each data transmitting and receiving device requesting a healthcare service; and
a server, said server communicates with each data transmitting and receiving device over a communication network, said server stores health related information for a plurality of patients, the server receives said geographic location of each data transmitting and receiving device, the server generates a visitation schedule of a healthcare provider based upon the health related information of each patient of said plurality of patients, said geographic location of each device, patient availability of each patient, a risk stratification of each patient, and any requests for healthcare service, the server further tracking patient compliance with a treatment program by comparing received geographic location data of a particular device with predetermined healthcare service location data.

2. The remote health monitoring system claimed in claim 1, further comprising a workstation, wherein said workstation communicates with said server.

3. The remote health monitoring system claimed in claim 2, wherein said workstation comprises at least of one of a personal computer, a handheld computer or a remote terminal.

4. The remote health monitoring system claimed in claim 1, further comprising a measuring apparatus suitable for measuring health related data and transmitting said health related data to said server via said communication network.

5. The remote health monitoring system claimed in claim 4, wherein said measuring apparatus measures at least one of a blood glucose level, a pulse, a weight, a blood pressure, or a peak flow.

6. The remote health monitoring system claimed in claim 1, wherein each data transmitting and receiving device is configured for receiving queries from said server, accepting a patient query response, and transmitting said patient query responses to said server.

7. The remote health monitoring system claimed in claim 6, wherein said visitation schedule is further determined by a web based traffic report and a web based weather report.

8. The remote health monitoring system claimed in claim 1, wherein said each transmitting and receiving device is configured to receive patient availability data.

9. The remote health monitoring system claimed in claim 1, wherein each of the at least two data transmitting and receiving devices reports geospatial position data to the server upon receipt of patient acknowledgement for patient privacy consideration.

10. The remote health monitoring system claimed in claim 1, wherein each of the at least two data transmitting and receiving devices provides a particular patient with information of a particular healthcare facility location based upon geographic location data of healthcare facilities and at least one of supply data of the healthcare facilities or service data of the healthcare facilities.

11. A remote health monitoring system, comprising:
at least two data transmitting and receiving devices, each data transmitting and receiving device of said at least two data transmitting and receiving devices includes a global positioning system receiver, said global positioning system receiver determines a geographic location of said device, each data transmitting and receiving device transmits said geographic location of said device, each data transmitting and receiving device being associated with a single patient and includes at least one actuator for data input for responding to a health related information query, each data transmitting and receiving device providing patient availability, and each data transmitting and receiving device requesting a healthcare service; and a server, said server communicates with each data transmitting and receiving device over a communication network, said server stores health related information for a plurality of patients, the server receives said geographic location of each data transmitting and receiving device, the server generates a visitation schedule of a healthcare provider based upon the health related information of each patient of said plurality of patients, said geographic location of each device, patient availability of each patient, a risk stratification of each patient, any requests for healthcare service, and healthcare facilities determined by the server to be in proximity to said geographical location of each device, the server further tracking patient compliance with a treatment program by comparing received geographic location data of a particular device with predetermined healthcare service location data.

12. The remote health monitoring system claimed in claim 11, further comprising a workstation, wherein said workstation communicates with said server.

13. The remote health monitoring system claimed in claim 12, wherein said workstation comprises at least of one of a personal computer, a handheld computer or a remote terminal.

14. The remote health monitoring system claimed in claim 11, further comprising a measuring apparatus suitable for measuring health related data and transmitting said health related data to said server via said communication network.

15. The remote health monitoring system claimed in claim 14, wherein said measuring apparatus measures at least one of a blood glucose level, a pulse, a weight, a blood pressure, or a peak flow.

16. The remote health monitoring system claimed in claim 11, wherein each data transmitting and receiving device is configured for receiving queries from said server, accepting a patient query response, and transmitting said patient query responses to said server.

17. The remote health monitoring system claimed in claim 11, wherein each data transmitting and receiving device is configured to receive patient availability data.

18. The remote health monitoring system claimed in claim 17, wherein said visitation schedule is further determined by a web based traffic report and a web based weather report.

19. The remote health monitoring system claimed in claim 11, wherein each of the at least two data transmitting and receiving devices reports geospatial position data to the server upon receipt of patient acknowledgement for patient privacy consideration.

20. The remote health monitoring system claimed in claim 11, wherein each of the at least two data transmitting and receiving devices provides a particular patient with information of a particular healthcare facility location based upon geographic location data of the healthcare facilities and at least one of supply data of the healthcare facilities or service data of the healthcare facilities.

* * * * *